(12) United States Patent
Haycraft et al.

(10) Patent No.: US 8,866,039 B1
(45) Date of Patent: Oct. 21, 2014

(54) LASER IGNITABILITY SYSTEMS AND METHODS

(75) Inventors: James Joseph Haycraft, Ridgecrest, CA (US); Kevin Paul Ford, Ridgecrest, CA (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 729 days.

(21) Appl. No.: 13/174,230

(22) Filed: Jun. 30, 2011

(51) Int. Cl.
*B23K 26/06* (2014.01)
*B23K 26/03* (2006.01)

(52) U.S. Cl.
USPC ............. 219/121.61; 219/121.73; 219/121.83

(58) Field of Classification Search
CPC ............... B23K 26/00; B23K 26/0626; B23K 26/0066; B23K 26/032; G02B 27/281
USPC ............. 219/121.61, 121.62, 121.68, 121.69, 219/121.73, 121.83
See application file for complete search history.

(56) References Cited

U.S. PATENT DOCUMENTS

| | | | | |
|---|---|---|---|---|
| 3,265,855 | A * | 8/1966 | Norton | 219/121.72 |
| 3,519,359 | A * | 7/1970 | Berg | 219/121.68 |
| 3,803,379 | A * | 4/1974 | McRay | 219/121.6 |
| 5,166,492 | A * | 11/1992 | Rivera | 219/121.68 |
| 5,737,132 | A * | 4/1998 | Luecke et al. | 359/822 |
| 5,852,519 | A * | 12/1998 | Do et al. | 359/822 |
| 6,191,848 | B1 * | 2/2001 | Armitage | 372/107 |
| 6,356,578 | B1 * | 3/2002 | Yin | 372/107 |
| 7,160,792 | B2 * | 1/2007 | Zhang et al. | 438/487 |
| 2003/0086451 | A1 * | 5/2003 | Hastings et al. | 372/29.014 |
| 2003/0231408 | A1 * | 12/2003 | Wolleschensky | 359/726 |
| 2005/0134950 | A1 * | 6/2005 | Morrow et al. | 359/212 |
| 2005/0286576 | A1 * | 12/2005 | Gill et al. | 372/29.021 |
| 2008/0240182 | A1 * | 10/2008 | Smith et al. | 372/29.021 |
| 2011/0242639 | A1 * | 10/2011 | Kleinert | 359/290 |

OTHER PUBLICATIONS

Blachowski et al., "CAD/PAD Laser Ignitability Programs at the Indian Head Division, Naval Surface Warfare Center",NAVSEA, Mar. 2010.*

* cited by examiner

*Primary Examiner* — Geoffrey S Evans
(74) *Attorney, Agent, or Firm* — Christopher L. Blackburn; James M. Saunders

(57) ABSTRACT

A laser system simulates heat flux levels of rocket motor output. A laser is mechanically associated with a platform. The laser is configured to emit an electromagnetic beam. A plurality of positions are associated with the platform. Optical elements are associated with the platform. Each optical element is positionable in a plurality of positions without changing a location of the corresponding positioner. The optical elements are arrangeable into a plurality of combinations corresponding to at least one optical path beginning at the laser and terminating at a sample. Each combination corresponds to one of a plurality of distinct permutations of operatively positioned optical elements that reducingly interact with an emitted electromagnetic beam, yielding one of many versions of the emitted electromagnetic beam that is incidented upon the sample. Each version of the emitted electromagnetic beam that is incidented upon the sample has a lower power than the emitted electromagnetic beam.

22 Claims, 8 Drawing Sheets

LASER IGNITABILITY SYSTEMS AND METHODS

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

Embodiments of the invention generally relate to an apparatus and process to experimentally simulate heat flux levels over several orders of magnitude using laser energy.

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

DETAILED DESCRIPTION OF EMBODIMENTS OF THE INVENTION

Embodiments of the invention generally relate to an apparatus and process to experimentally simulate heat flux levels over several orders of magnitude using an appropriate laser and a single optical setup.

Embodiments of the invention allow for a single optical train (with removable/adjustable/rotatable optical components) to study a plurality of operating conditions by collecting/generating ignitability data over a plurality of flux levels (in some embodiments, the flux levels include flux spectrums that that includes, for example, a higher flux regime (simulate a rocket motor igniter output) and lower flux regimes) to better predict more accurate time to ignition for hazards scenarios. The invention allows for a single optical train to study a large range of operating conditions. In some of these embodiments, the laser is not pulsed. The optical train allows for a definitive measure of the heat flux it radiates on a target sample without replacing the sample with an instrument to measure the flux.

Some of the embodiments described herein describe an optical train that allows for both high and low flux regimes to be examined using a single system. However, it is contemplated that some embodiments of the invention are operable to reduce to reduce the power of beams at a sample from a higher power region of a flux regime to a lower power of the same flux regime.

FIGS. 1-4 illustrate various combinations of optical elements 8, 9 in a single optical train in accordance with principles of the invention. FIGS. 5-8 illustrate various combinations of optical elements 8, 9 in a single optical train. In these illustrations, of the optical elements 8, 9 associated with an optical train, only the operatively positioned optical elements 8, 9 are illustrated. Each of the principle electromagnetic ("EM") beams (designated by reference number 6 and represented using a solid line) in FIGS. 1-4 use the same path as the principle EM beams in the others of FIGS. 1-4. Each of the principle EM beams 6 in FIGS. 5-8 use the same path as the principle EM beams 6 in the others of FIGS. 5-8 and a different path than the principle EM beams 6 of FIGS. 1-4.

Figure 5:
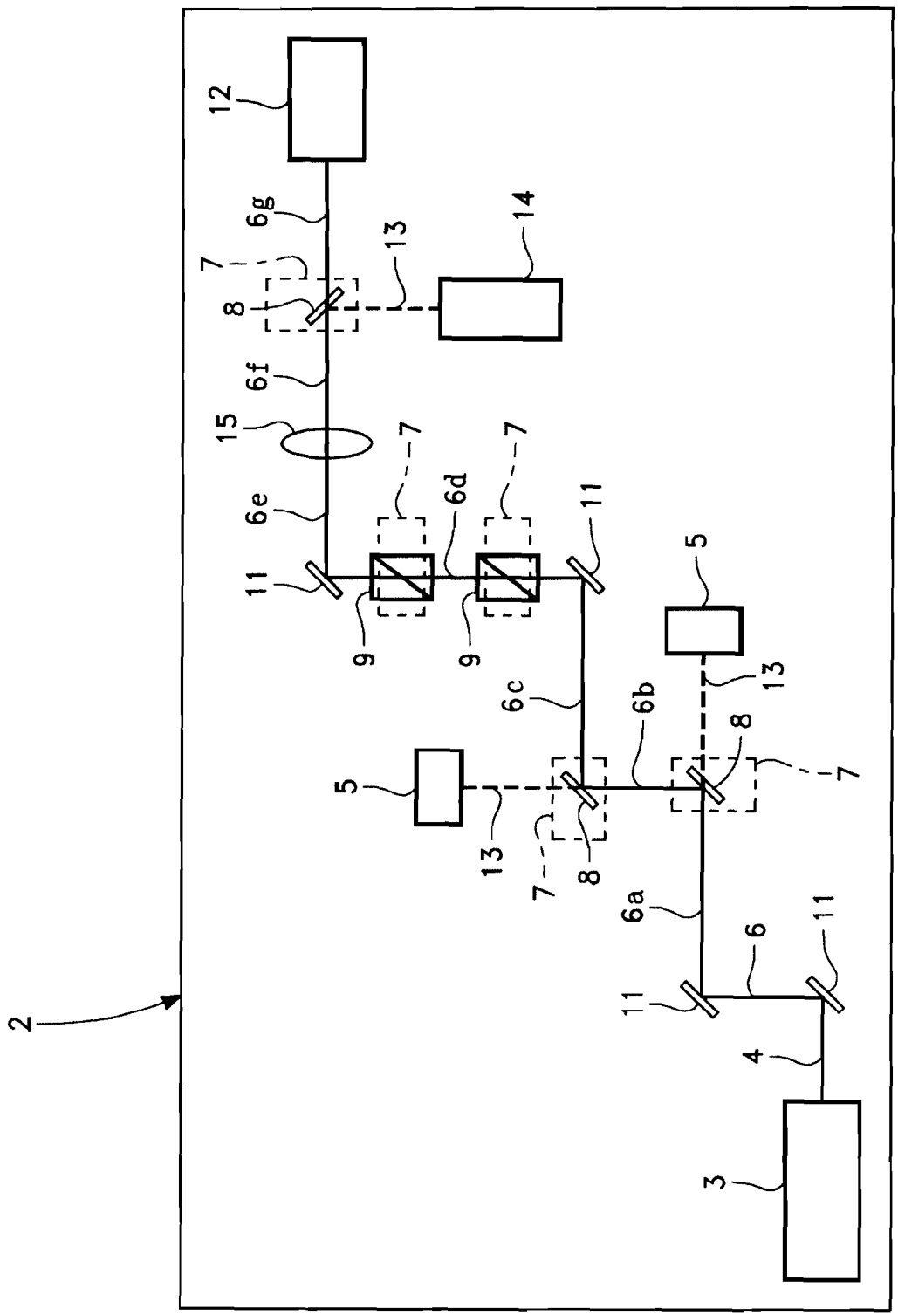
FIG. 5 illustrates a plan view of an embodiment of a system according to principles of the invention.
Figure 6:
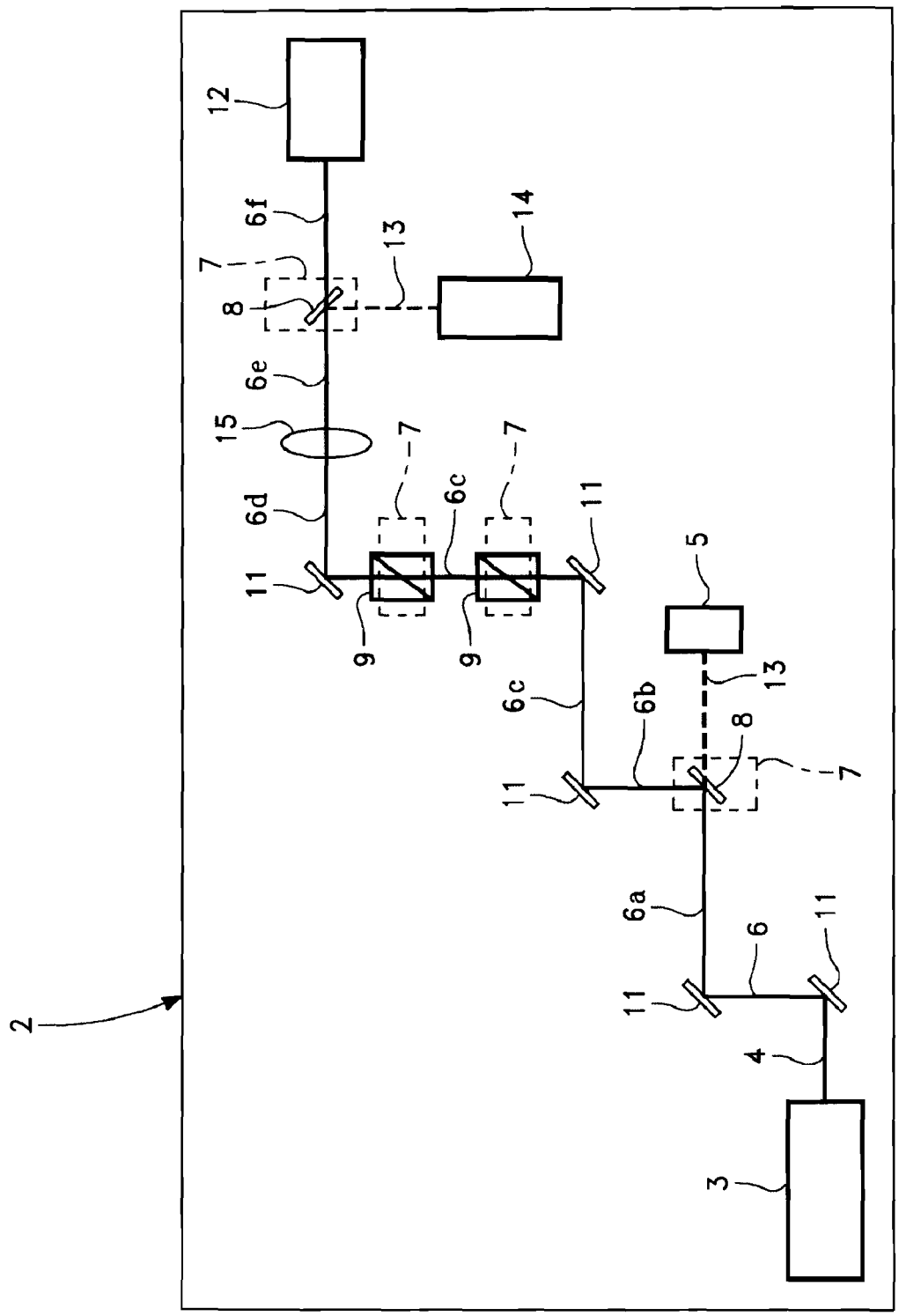
FIG. 6 illustrates a plan view of an embodiment of a system according to principles of the invention. In this figure, the second optical element in FIG. 5 is rotated out of the principle EM beam system path (and replaced with a mirror). This figure illustrates a system that employs the same EM beam system path as FIG. 5. This figure illustrates a system that, if active, would produce a principle EM beam incident on the sample having a lower power than the power of the principle EM beam incident on the sample of FIG. 5.
Figure 7:
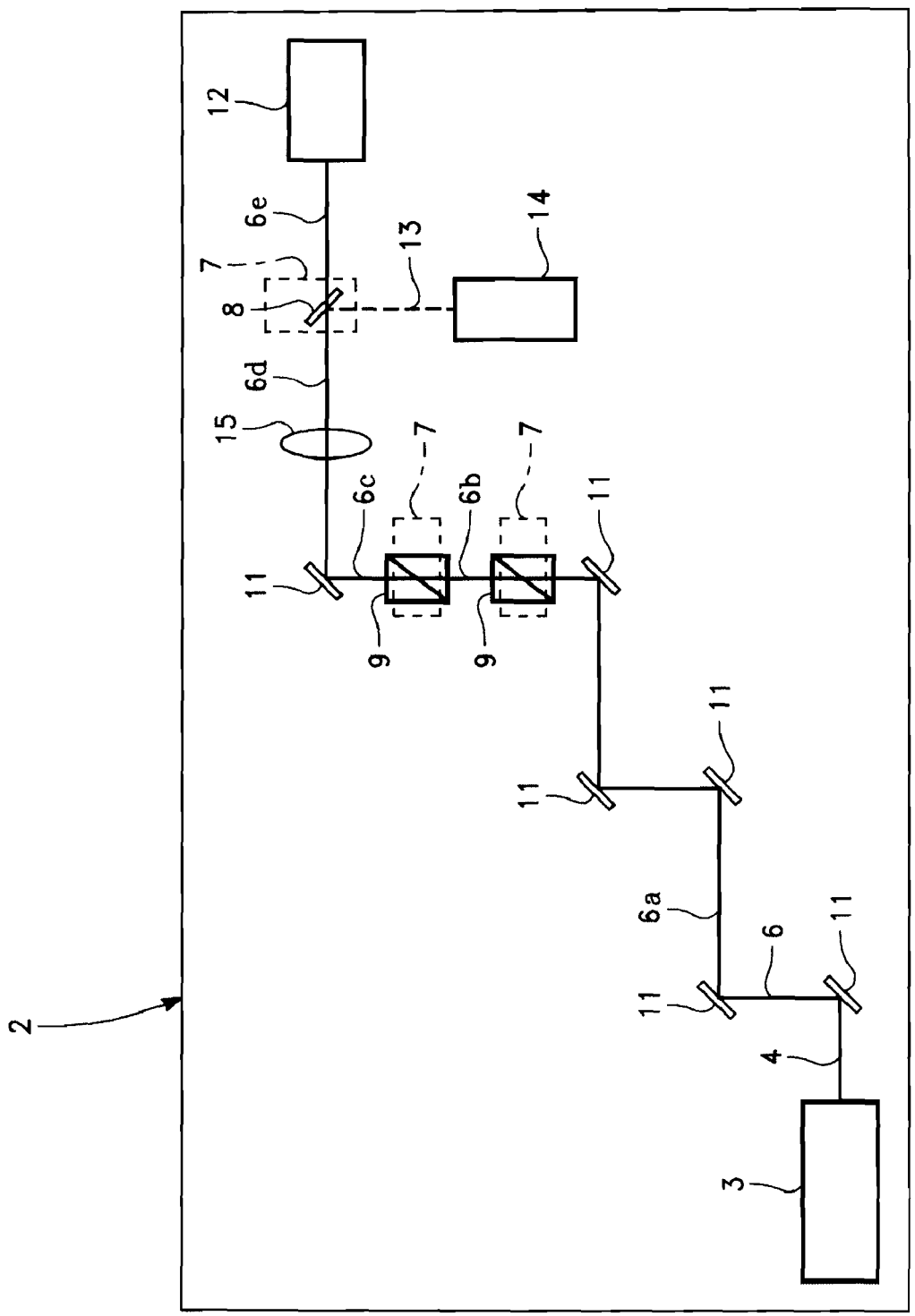
FIG. 7 illustrates a plan view of an embodiment of a system according to principles of the invention. In this figure, the first and second optical elements in FIG. 5 are rotated out of the principle EM beam system path (and replaced with a mirror). This figure illustrates a system that employs the same EM beam system path as FIG. 5. This figure illustrates a system that, if active, would produce a principle EM beam incident on the sample having a lower power than the power of the principle EM beam incident on the sample of FIGS. 5 and 6.
Figure 8:
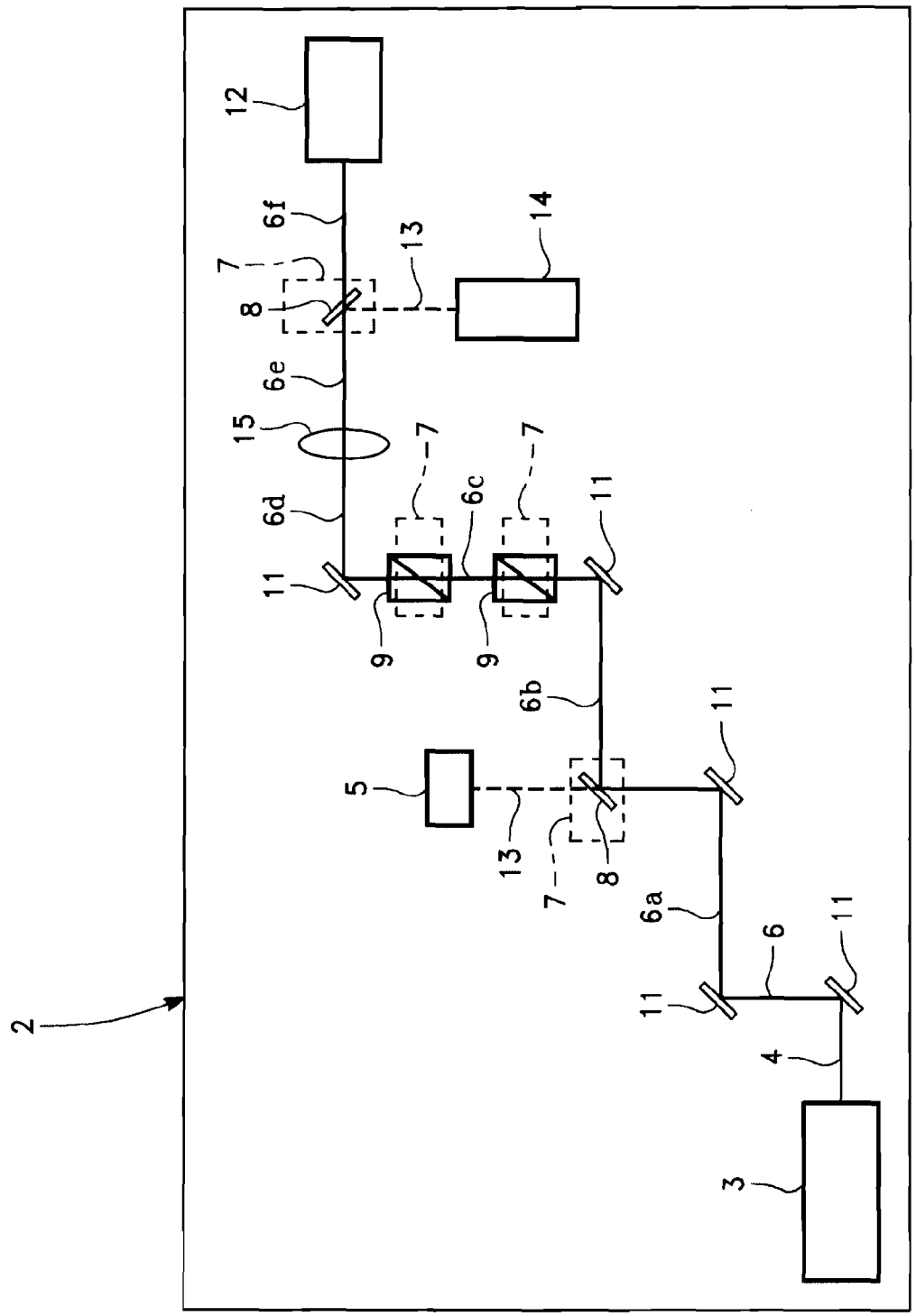
FIG. 8 illustrates a plan view of an embodiment of a system according to principles of the invention. In this figure, the first optical element in FIG. 5 is rotated out of the principle EM beam system path (and replaced with a mirror). This figure illustrates a system that employs the same EM beam system path as FIG. 5. This figure illustrates a system that, if active, would produce a principle EM beam incident on the sample having a lower power than the power of the principle EM beam incident on the sample of FIG. 5.

Further, in some embodiments, such as can be exemplarily seen from FIGS. 5 and 6, at least some of the beamsplitter(s) 8 are interchangeably replaceable with a mirror (such as the second beamsplitter 8 in the useable EM beam system path of FIG. 5 being replaced with a mirror 11 in the useable EM beam system path of FIG. 6)—though the mirror is not considered to be an 'optical element', in part because the mirror 11 does not serve to reduce the power of the beam it emanates.

With reference to FIGS. 1-8, embodiments of the invention include a platform 2. As used in this specification, including the claims, a platform 2 is a piece of equipment used for optics experiments and engineering. In optical setups, the alignment of each component must be extremely accurate—precise down to a fraction of a wavelength. The surface of the platform 2 is sufficiently flat to allow precision optical mounts 7 to make good contact with the platform 2 without rocking. In some embodiments, the platform 2 is an 'optical table'. In other embodiments, the platform 2 is an optical bench or rail. In yet other embodiments, the platform 2 is an optical breadboard.

Embodiments of the invention further include a laser 3 to emit an electromagnetic beam 4; the laser 3 is associated with the platform 2. In some embodiments, the laser 3 is associated with the platform 2 using a fastener. In other embodiments, the laser 3 is associated with the platform 2 using magnetic force. The laser 3 can be any type of laser ranging from ultraviolet to infrared. In some embodiments, the laser 3 is a $CO_2$ laser. The laser 3 emits radiation that propagates along a path(s), described below.

Some embodiments include beam steering optics 11 associated with the platform and used to correctly align the radiation emitted from the laser with the optical table.

The embodiments include at least one optical element 8, 9 rotatably associated with the platform 2 using a positioner 7 such that each of said plurality of optical elements 8, 9 is positionable in a plurality of positions without changing a location of its corresponding positioner 7. One of the plurality of positions is an 'operative position' and another of the plurality of positions is an 'inoperative position'. When in an 'inoperative position' the optical element 8, 9 does not interact with principle EM beams 6. When in an 'operative position', the optical element 8, 9 interacts with principle EM beam(s) 6 along at least one of a pre-determined principle EM beam system paths.

Figure 1:
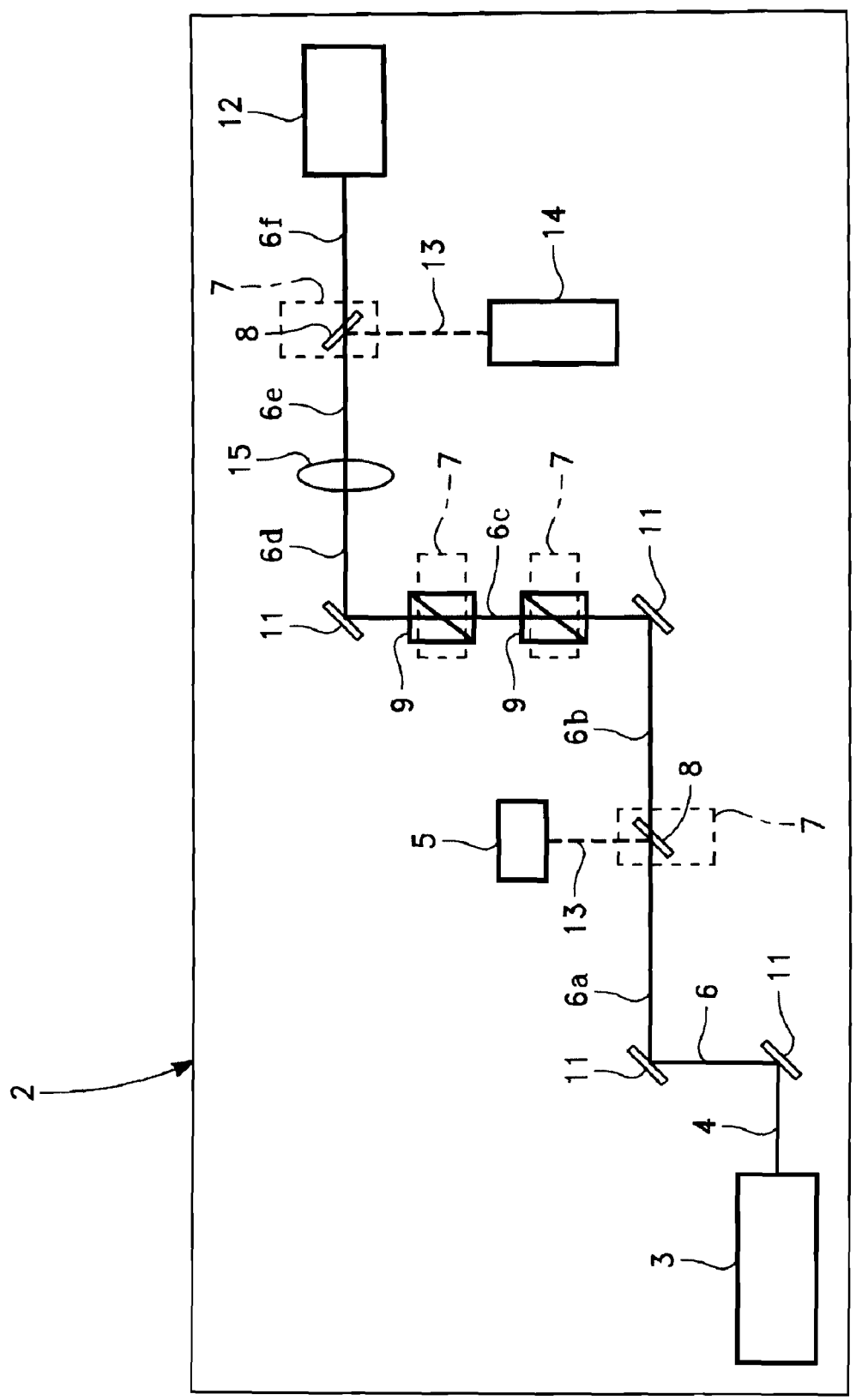
FIG. 1 illustrates a plan view of an embodiment of a system according to principles of the invention.
Figure 2:
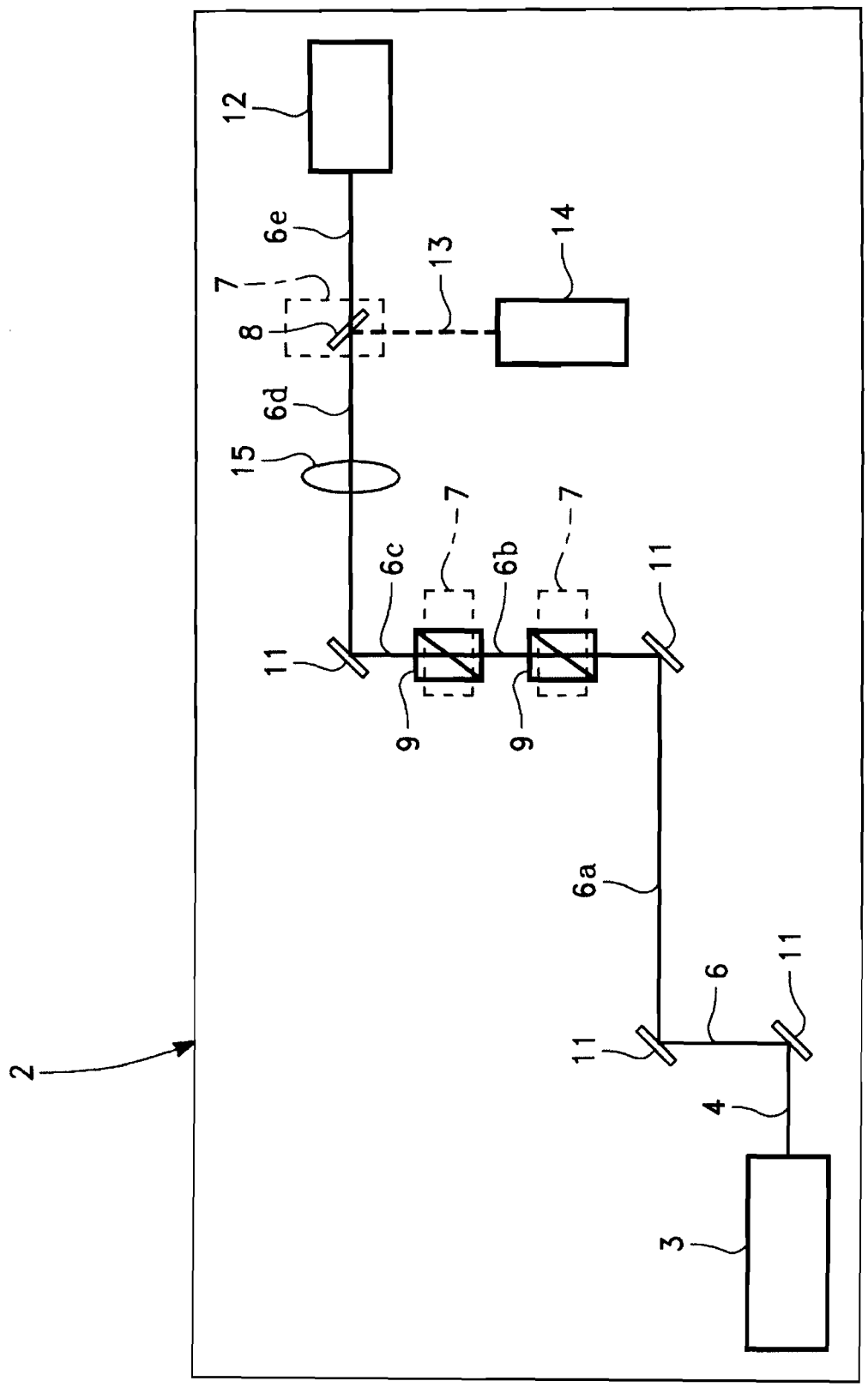
FIG. 2 illustrates a plan view of an embodiment of a system according to principles of the invention. In this figure, the first optical element in FIG. 1 is rotated out of the principle EM beam system path. This figure illustrates a system that employs the same EM beam system path as FIG. 1. This figure illustrates a system that, if active, would produce a principle EM beam incident on the sample having a lower power than the power of the principle EM beam incident on the sample of FIG. 1.
Figure 3:
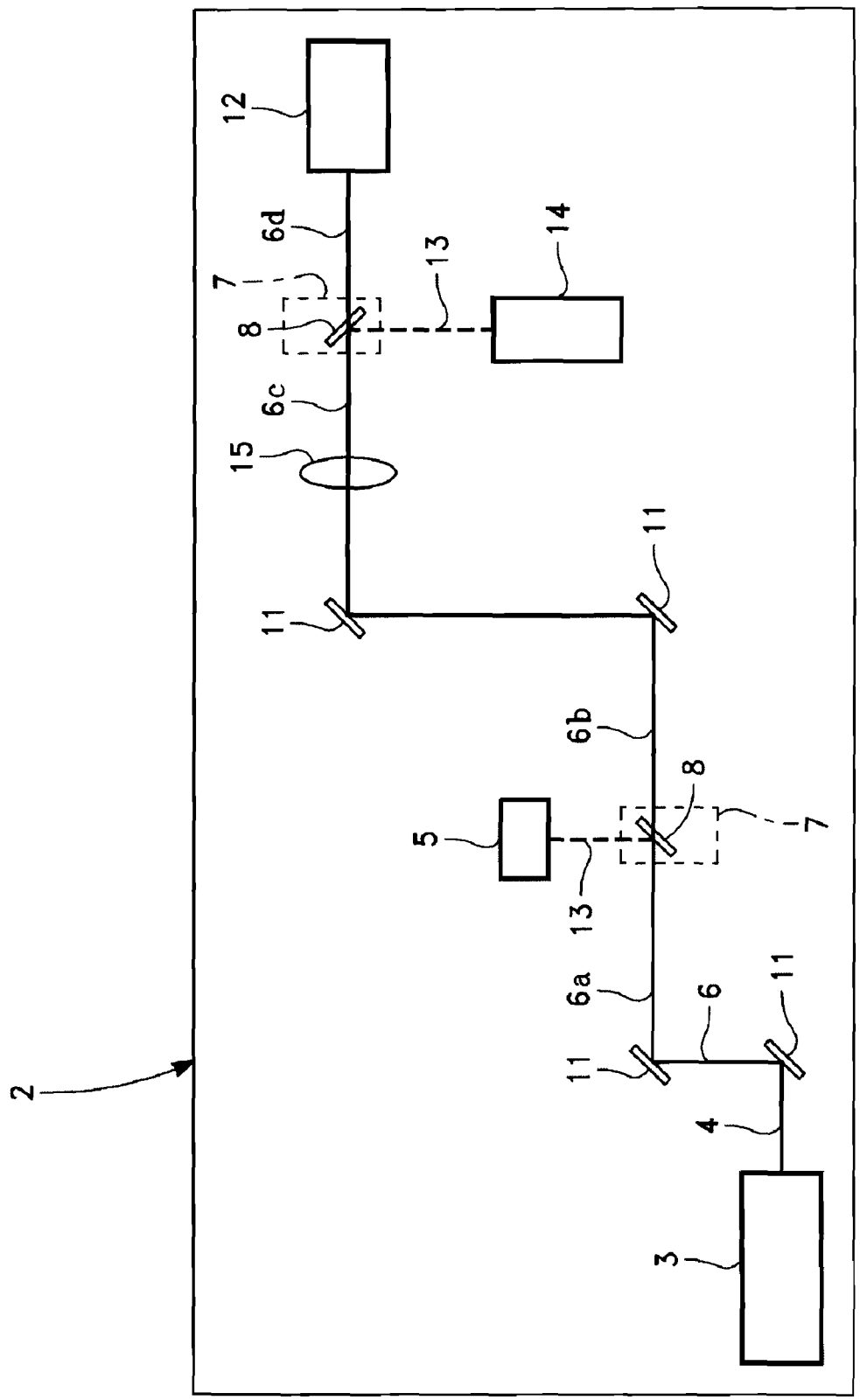
FIG. 3 illustrates a plan view of an embodiment of a system according to principles of the invention. In this figure, the polarizing optical elements in FIG. 1 is rotated out of the principle EM beam system path. This figure illustrates a system that employs the same EM beam system path as FIG. 1. This figure illustrates a system that, if active, would produce a principle EM beam incident on the sample having a lower power than the power of the principle EM beam incident on the sample of FIG. 1.
Figure 4:
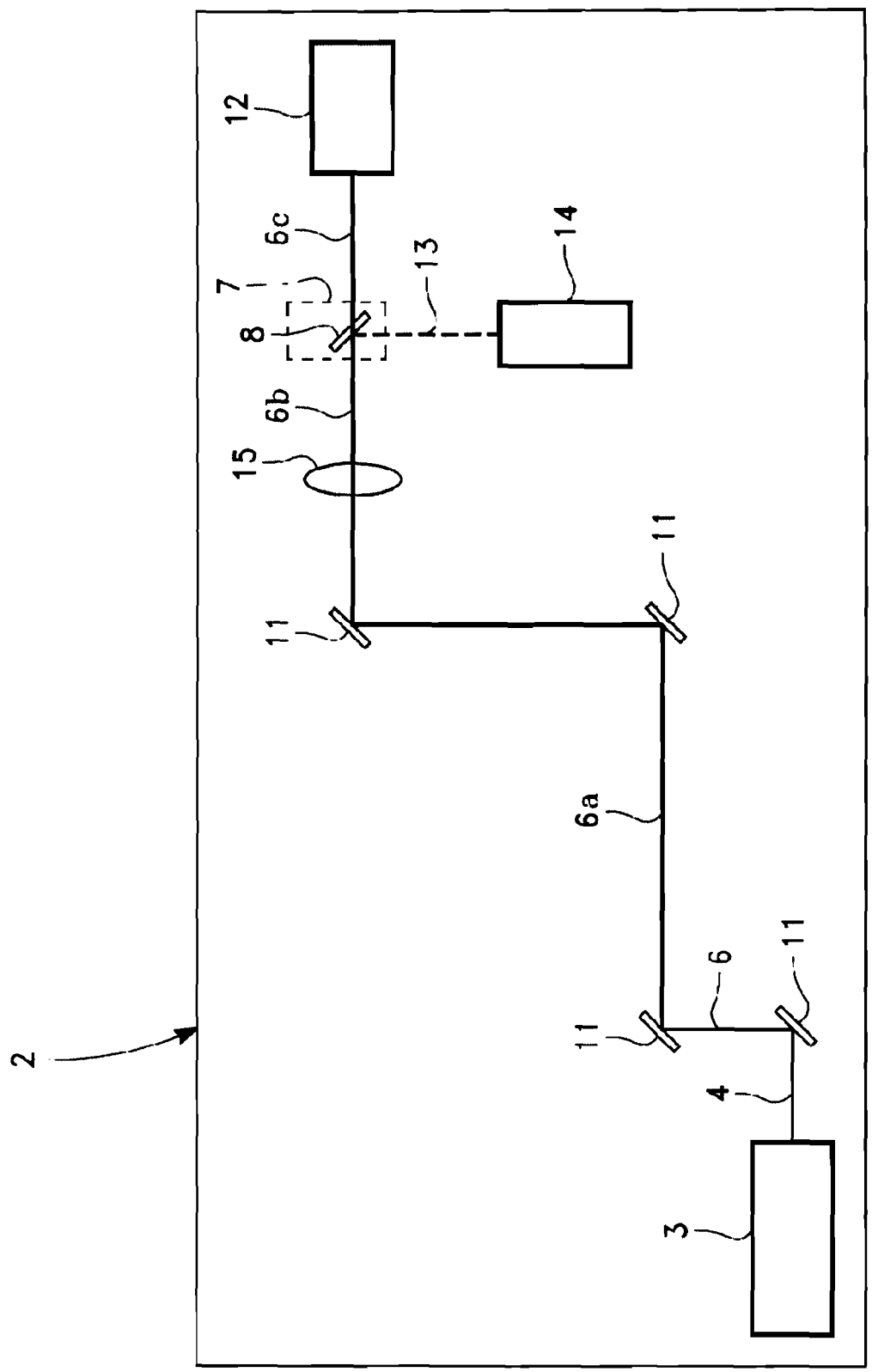
FIG. 4 illustrates a plan view of an embodiment of a system according to principles of the invention. In this figure, the first optical element in FIG. 1, as well as the polarizing optics in FIG. 1, are rotated out of the principle EM beam system path. This figure illustrates a system that employs the same EM beam system path as FIG. 1. This figure illustrates a system that, if active, would produce a principle EM beam incident on the sample having a lower power than the power of the principle EM beam incident on the sample of FIGS. 1, 2, and 3.

The term 'optical element' 8, 9 as used herein, including the claims, is defined as an optical element 8, 9 selected from the group of optical elements consisting of: polarizing optics 9 and beamsplitters 8. With reference to FIGS. 3-4, in some embodiments, the at least one optical element 8, 9 includes at least one beamsplitter 8. With reference to FIGS. 1, 2, and 5-8, in other embodiments, the at least one optical element 8, 9 includes at least one beamsplitter 8 and at least one polarizing optic 9.

With reference to FIGS. 1-8, each of the at least one optical elements 8, 9 is rotatable into (and out of) at least one of the at least one principle EM beam system paths (designated using 6)—the plurality of optical elements 8, 9 being arrangeable into a plurality of combinations with each of the plurality of combinations corresponding to one of at least one principle EM beam system path 6 beginning at the laser 3 and terminating at a sample 12. Each of the plurality of combinations corresponding to one of a plurality of distinct permutations of operatively positioned optical elements 8, 9 that reducingly interact with an emitted EM beam 4 (along at least one of a pre-determined number of principle EM beam system paths) thereby yielding one of a plurality of versions of the emitted EM beam 4 that is incidented upon the sample 12, with each of the plurality of versions of the emitted of the EM beam 4 that is incidented upon the sample (6f in FIGS. 1, 6, and 8; 6e in FIGS. 2 and 7; 6d in FIG. 3; 6c in FIG. 4, 6g in FIG. 5) having a lower power than the emitted EM beam 4.

Note that in some embodiments, the emitted EM beam 4 has a power within an upper region of a first flux regime, and at least one of the plurality of versions of the emitted beam incident on the sample (6f in FIGS. 1, 6, and 8; 6e in FIGS. 2 and 7; 6d in FIG. 3; 6c in FIG. 4, 6g in FIG. 5) has a power at the sample that is within a lower region of the first flux regime.

A principle EM system beam path is used herein, including the claims, to describe an optical path, given the combination of operatively positioned optical elements 8, 9, that begins at the laser 3 and terminates at a sample 12 (a principle EM beam system path is indicated using the line illustrating a principle EM beam 6). Each principle EM system beam paths describes the optical path in which a principle EM beams 6 travels (an associated of the at least one principle EM beam system paths). A principle EM beam 6 is derived from the emitted electromagnetic beam 4 and describes a beam that, when the system is used (active), travels from the laser 3 to the sample 12. Each of the at least one principle EM beam 6 is formed of one of a plurality of series of usable series electromagnetic beams (6a-g). In use, each of the at least one optical elements 8, 9 that is rotated into one of the at least one principle EM beam system paths associated with an active of at least one of the at least one principle EM beams 6 receives one of the usable series electromagnetic beams (6a-f) and emanates one of the usable series electromagnetic beams (6a-f). Each of the at least one optical element 8, 9 that is rotated into one of the at least one principle EM beam system paths associated with an active of at least one of the at least one principle EM beams 6 reduces the power of the usable series electromagnetic beam (6a-f) the optical element 8, 9 emanates relative to the power of the usable series electromagnetic beam (6a-f) the optical element 8, 9 receives.

In some embodiments, the at least one optical element(s) (8 and 9 in FIGS. 1-8, where present) is rotatably associated with the platform 2 using precision flip mounts 7; however, other mechanisms and principles can be used in accordance with embodiments of the invention. In embodiments in which a flip mount 7 is used to rotatably associate the at least one optical element 8, 9 to the platform 2, the optical element 8, 9 is associated with the platform 2 via the flip mount 7 such that the optical element 8, 9 can be removed from the principle EM beam path by rotating the flip mount 7 in one direction; conversely, the optical element 8, 9 can be rotated into the principle EM beam path to reduce the power of the principle EM beam 6 by rotating the flip mount 7 in another direction.

In embodiments that use a beamsplitter 8 as an optical element 8, 9, each beamsplitter 8 that is rotated into an active of the at least one usable series EM beams 6 splits the usable series electromagnetic beams (group including 6a-g) the beamsplitter 8 receives into a plurality of split beams, wherein the plurality of split beams includes the usable series electromagnetic beam 6 the optical element 8, 9 emanates (having a reduced power relative to the principle series EM beam the optical element 8, 9 received) and a secondary EM beam 13.

In some embodiments, the principle EM beam system path is influenced using beam steering optics 11 associated with the platform 2.

As illustrated in FIGS. 1, 3, 5, 6, and 8, some embodiments that include a beamsplitter 8 also include at least one beam block 5 located and adapted to absorb the secondary EM beam 13.

In some embodiments, the emitted electromagnetic beam 4 has a power within a first flux regime, wherein the first flux regime is a flux regime having a greater minimum power than a maximum value of a second flux regime. In some embodiments, the first and second flux regimes are selected from the group of regimes consisting of:

Region 1=Ultra-High Flux=Above 8000 kW/m2

Region 2=Igniter Response Regime=1000 to 8000 kW/m2

Region 3=Combustion Regime=400 to 1000 kW/m2

Region 4=Fast Cook-off Regime=40 to 400 kW/m2

Region 5=Slow Cook-off Regime=Less than 40 kW/m2

Every permutation of flux regimes that is consistent with the principles of the invention is contemplated. For example, in some embodiments, the first flux regime is Region 1 and the second flux regime is Region 2. In other embodiments, the first flux regime is Region 1 and the second flux regime is Region 3. In other embodiments, the first flux regime is Region 1 and the second flux regime is Region 4. In other embodiments, the first flux regime is Region 1 and the second flux regime is Region 5. In other embodiments, the first flux regime is Region 2 and the second flux regime is Region 3. In other embodiments, the first flux regime is Region 2 and the second flux regime is Region 4. In other embodiments, the first flux regime is Region 2 and the second flux regime is Region 5. In other embodiments, the first flux regime is Region 3 and the second flux regime is Region 4. In other embodiments, the first flux regime is Region 3 and the second flux regime is Region 5. In other embodiments, the first flux regime is Region 4 and the second flux regime is Region 5. It is noted that the number of flux regimes from which the first and second flux regime are selected, as well as the power levels for the different regimes, provided above is exemplary; the number of flux regimes, as well as the power levels for the different regimes, can vary according to scientifically accepted definitions of varying flux regimes used in the technological field in which the system is used.

In some of the embodiments in which the at least one optical element 8, 9 includes at least one beamsplitter, one of the at least one beamsplitters 8 is a last optical element 8, 9 that the principle EM beam 6 travels through prior to being incident on the sample 12. In use, the secondary EM beam 13 split off by the last of the at least one beamsplitters 8 is directed to an optical detector 14. The optical detector 14 and sample 12 are both connected to a data acquisition instrument. The data acquisition instrument can be any electronic instrument that records output from the sample and detector as a function of time and allows for precise determination of onset of reaction.

Some embodiments include a focusing optic 15 rotatably associated with the platform 2 and rotatable into and out of the principle EM beam system path.

Inter-Regime Method

Some embodiments of a method of testing a sample 12 include emitting an electromagnetic beam 4 from a laser 3 mechanically associated with a platform 2.

These method embodiments further include incidenting a first principle EM beam 6 derived from the emitted EM beam 4 onto a sample 12, the first principle EM beam 6 having a power at the sample 12 within a power region of a first flux regime of a plurality of flux regimes. The first principle EM beam 12 propagates along one of at least one principle EM beam system paths onto a sample 12 and is derived from the emitted EM beam 6 passing through a first optical element 8, 9 combination of a plurality of optical element 8, 9 combinations; the plurality of optical element 8, 9 combinations is formed using a plurality of optical elements 8, 9 rotatably associated with the platform 2 such that each of the plurality of optical elements 8, 9 is rotatable into and out at least one of the at least one principle EM beam system paths.

These method embodiments further include rearranging at least one of the plurality of optical elements 8, 9 to form one of at least one reduced power optical element 8, 9 combinations and yielding at least one reduced power principle EM beams 6 that propagates along at least one of the principle EM beam system paths (in some embodiments, the same path as the path that the first principle EM beam 6 travels) and terminates at the sample 12, at least one of the at least one reduced power principle EM beams 6 having a power incident at the sample 12 within a reduced power flux regime of the plurality of flux regimes, the reduced power flux regime having a lower power than the first flux regime.

Some method embodiments include performing the rearranging step a plurality of times during a testing of the sample 12, wherein each performance of the rearranging step uses one of the at least one reduced power optical element 8, 9 combinations that has not been used during the testing of the sample 12, wherein each of the plurality of performances of the rearranging step yields one of a plurality of the at least one reduced power principle EM beams 6 that propagates along one of the at least one principle EM beam system paths and terminates at the sample 12; each of the plurality of the at least one reduced power principle EM beams 6 has a power within a single of a plurality of reduced power flux regimes. Each one of the plurality of the at least one reduced power principle EM beams 6 has a power incident on the sample 12 that is within a different of the plurality of reduced power flux regimes than each other one of the plurality of the at least one reduced power principle EM beams 6, wherein each of the plurality of reduced power flux regimes has a lower power than the first flux regime.

In some embodiments, the power of the first principle EM beam 6 at the sample 12 is equal to the power of the emitted EM beam 4.

In some embodiments the first flux regime is Region 1=Ultra-High Flux=Above 8000 kW/m2 and the reduced power flux regime is selected from the group of flux regimes consisting of: Region 2=Igniter Response Regime=1000 to 8000 kW/m2, Region 3=Combustion Regime=400 to 1000 kW/m2, Region 4=Fast Cook-off Regime=40 to 400 kW/m2, and Region 5=Slow Cook-off Regime=Less than 40 kW/m2.

In some embodiments the first flux regime is Region 2=Igniter Response Regime=1000 to 8000 kW/m2 and the reduced power flux regime is selected from the group of flux regimes consisting of: Region 3=Combustion Regime=400 to 1000 kW/m2, Region 4=Fast Cook-off Regime=40 to 400 kW/m2, and Region 5=Slow Cook-off Regime=Less than 40 kW/m2.

In some embodiments the first flux regime is Region 3=Combustion Regime=400 to 1000 kW/m2 and the reduced power flux regime is selected from the group of flux regimes consisting of: Region 4=Fast Cook-off Regime=40 to 400 kW/m2, and Region 5=Slow Cook-off Regime=Less than 40 kW/m2.

In some embodiments the first flux regime is Region 4=Fast Cook-off Regime=40 to 400 kW/m2 and the reduced power flux regime is Region 5=Slow Cook-off Regime=Less than 40 kW/m2.

In some embodiments, each one of the plurality of reduced power flux regimes is selected from the group of flux regimes consisting of: Region 2=Igniter Response Regime=1000 to 8000 kW/m2, Region 3=Combustion Regime=400 to 1000 kW/m2, Region 4=Fast Cook-off Regime=40 to 400 kW/m2, Region 5=Slow Cook-off Regime=Less than 40 kW/m2.

In some of these method embodiments, at least one of the at least one optical element 8, 9 is a beamsplitter 8, wherein the beamsplitter 8 is a last optical element 8, 9 that the first principle EM beam 6 and each of the at least one reduced power principle EM beam travel 6 through prior to being incident on the sample 12. In these embodiments, some methods include directing a secondary beam 13 (which is formed of a pre-determined amount of the first principle EM beam 6) toward an optical detector 14 using the beamsplitter 8, measuring the power of the secondary beam 13 received at the optical detector 14, and determining the power of the first principle EM beam 6 incident on the sample 12 by using a mathematical relation of the power of the secondary beam 13 to an amount of the first principle EM beam 6 incident on the sample 12. Some of these methods further include: directing a secondary beam 13 (which is formed of a pre-determined amount of a reduced power principle EM beam 6) toward the optical detector 14 using the beamsplitter 8; measuring the power of the pre-determined amount of the secondary beam 13 received at the optical detector 14; and determining the power of the at least one reduced power principle EM beams 6 incident on the sample 12 by using a mathematical relation of the amount of the pre-determined amount of the secondary beam 13 directed toward the optical detector 14 and the amount of the reduced power principle EM beam 6 incident on the sample 12.

Intra-Regime Method

Some embodiments of a method of testing a sample 12 include emitting an electromagnetic beam 4 from a laser 3 mechanically associated with a platform 2.

These method embodiments further include incidenting a first (not order specific) principle EM beam 6 derived from the emitted EM beam 4 onto a sample 12, the first principle EM beam 6 having a power at the sample 12 within a first power region of a first flux regime of a plurality of flux regimes, the first principle EM beam 6 propagating along one of at least one principle EM beam system paths onto a sample 12 and being derived from the emitted EM beam 6 passing through a first optical element 8, 9 combination of a plurality of optical element 8, 9 combinations; the plurality of optical element 8, 9 combinations formed using a plurality of optical elements 8, 9 rotatably associated with the platform 2 such that each of the plurality of optical elements 8, 9 is rotatable into and out at least one of the at least one principle EM beam system paths.

Method embodiments further include rearranging at least one of the plurality of optical elements 8, 9 to form one of at least one reduced power optical element 8, 9 combinations and yielding at least one reduced (relative to the first principle EM beam 6) power principle EM beams 6 that propagates along at least one of the principle EM beam system paths and terminates at the sample 12. At least one of the at least one reduced power principle EM beams 6 has a power incident at the sample 12 within a reduced power region of the first flux regime, the high end of the reduced power region having a lower power than the power of the lower end of the first region of the first flux regime. In some embodiments, the first region of the first flux regime is within the upper third of the range of the first flux regime and the reduced power region of the first flux regime is within the lower third of the range of the first flux regime; in some embodiments, the first flux regime is within the upper fourth of the range of the first flux regime and the reduced power region of the first flux regime is within the lower fourth of the range of the first flux regime.

In some of these method embodiments, at least one of the at least one optical element 8, 9 is a beamsplitter 8, wherein the beamsplitter 8 is a last optical element 8, 9 that at least one of the reduced power principle EM beams 6 travel through prior to being incident on the sample 12. In these embodiments, some methods include directing a secondary beam 13 (formed of a pre-determined amount of the first principle EM beam 6) toward an optical detector 14 using the beamsplitter 8, measuring the power of the secondary beam 13 received at the optical detector 14, and determining the power of the first principle EM beam 6 incident on the sample 12 by using a mathematical relation of the amount of the secondary beam 13 received at the optical detector 14 to an amount of the first principle EM beam 6 incident on the sample 12. Some of these methods further include: directing a secondary beam (formed of a pre-determined amount of the at least one reduced power principle EM beams 6) toward the optical detector 14 using the beamsplitter 8; measuring the power of the pre-determined amount of the secondary beam 13 received at the optical detector 14; and determining the power of the at least one reduced power principle EM beams 6 incident on the sample by using a mathematical relation of the amount of the pre-determined amount of the secondary beam 13 received at the optical detector 14 and the amount of the reduced power principle EM beam 6 incident on the sample 12.

Intra-Regime and Inter-Regime Method

Some embodiments of a method of testing a sample 12 include emitting an electromagnetic beam 4 from a laser 3 mechanically associated with a platform 2.

These method embodiments further include incidenting a first principle EM beam 6 derived from the emitted EM beam 4 onto a sample 12, the first principle EM beam 6 having a power at the sample 12 within a first power region of a first flux regime of a plurality of flux regimes, the first principle EM beam 12 propagating along one of at least one principle EM beam system paths onto a sample 12 and being derived from the emitted EM beam 6 passing through a first optical element 8, 9 combination of a plurality of optical element 8, 9 combinations; the plurality of optical element 8, 9 combinations formed using a plurality of optical elements 8, 9 rotatably associated with the platform 2 such that each of the plurality of optical elements 8, 9 is rotatable into and out at least one of the at least one principle EM beam system paths.

Some method embodiments further include rearranging at least one of the plurality of optical elements 8, 9 to form one of at least one reduced power optical element 8, 9 combinations and yielding at least one intra-flux reduced power principle EM beams that propagates along at least one of the principle EM beam system paths and terminates at the sample, at least one of the at least one intra-flux reduced power principle EM beams having a power incident at the sample that is within a reduced power region of the first flux regime, the high end of the reduced power region having a lower power than the power of the lower end of the first region of the first flux regime. In some embodiments, the first region of the first flux regime is within the upper third of the range of the first flux regime and the reduced power region of the first flux regime is within the lower third of the range of the first flux regime; in some embodiments, the first flux regime is within the upper fourth of the range of the first flux regime and the reduced power region of the first flux regime is within the lower fourth of the range of the first flux regime.

These method embodiments further include rearranging at least one of the plurality of optical elements 8, 9 to form one of at least one reduced power optical element 8, 9 combinations and yielding at least one inter-flux reduced power principle EM beams that propagates along at least one of the principle EM beam system paths and terminates at the sample, at least one of the at least one inter-flux reduced power principle EM beams having a power incident at the sample within a reduced power flux regime of the plurality of flux regimes, the reduced power flux regime having a lower power than the first flux regime.

In some embodiments the first flux regime is Region 1=Ultra-High Flux=Above 8000 kW/m2 and the reduced power flux regime is selected from the group of flux regimes consisting of: Region 2=Igniter Response Regime=1000 to 8000 kW/m2, Region 3=Combustion Regime=400 to 1000 kW/m2, Region 4=Fast Cook-off Regime=40 to 400 kW/m2, and Region 5=Slow Cook-off Regime=Less than 40 kW/m2.

In some embodiments the first flux regime is Region 2=Igniter Response Regime=1000 to 8000 kW/m2 and the reduced power flux regime is selected from the group of flux regimes consisting of: Region 3=Combustion Regime=400 to 1000 kW/m2, Region 4=Fast Cook-off Regime=40 to 400 kW/m2, and Region 5=Slow Cook-off Regime=Less than 40 kW/m2.

In some embodiments the first flux regime is Region 3=Combustion Regime=400 to 1000 kW/m2 and the reduced power flux regime is selected from the group of flux regimes consisting of: Region 4=Fast Cook-off Regime=40 to 400 kW/m2, and Region 5=Slow Cook-off Regime=Less than 40 kW/m2.

In some embodiments the first flux regime is Region 4=Fast Cook-off Regime=40 to 400 kW/m2 and the reduced power flux regime is Region 5=Slow Cook-off Regime=Less than 40 kW/m2.

In some embodiments, each one of the plurality of reduced power flux regimes is selected from the group of flux regimes consisting of: Region 2=Igniter Response Regime=1000 to 8000 kW/m2, Region 3=Combustion Regime=400 to 1000 kW/m2, Region 4=Fast Cook-off Regime=40 to 400 kW/m2, Region 5=Slow Cook-off Regime=Less than 40 kW/m2.

In some of these method embodiments, at least one of the at least one optical element 8, 9 is a beamsplitter 8, wherein the beamsplitter 8 is a last optical element 8, 9 that the emitted EM beam, and each of the at least one intra-flux reduced power principle EM beam 6 and inter-flux reduced power principle EM beam 6, travel 6 through prior to being incident on the sample 12. In these embodiments, some methods include directing a secondary beam 13 (formed of a predetermined amount of the at least one intra-flux reduced power principle EM beam 6) toward an optical detector 14 using the beamsplitter 8, measuring the power of the secondary beam 13 received at the optical detector 14, and determining the power of the intra-flux reduced power principle EM beam 6 incident on the sample 12 by using a mathematical relation of the amount of the secondary beam 13 directed toward the optical detector and the amount of the intra-flux reduced power principle EM beam 6 incident on the sample 12. Some of these methods further include: directing a predetermined amount of a secondary beam 13 (formed of the at least one inter-flux reduced power principle EM beams 6) toward the optical detector 14 using the beamsplitter 8; measuring the power of the secondary beam 13 received at the optical detector 14; and determining the power of the at least one inter-flux reduced power principle EM beams 6 incident on the sample 12 by using a mathematical relation of the amount of the secondary beam 13 directed toward the optical detector and the amount of the inter-flux reduced power principle EM beam 6 incident on the sample 12.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

The invention claimed is:

1. A laser system for simulating heat flux levels associated with rocket motor igniter output, comprising:
   a platform;
   a laser to emit an electromagnetic beam, said laser mechanically associated with said platform, wherein said laser is not pulsed;
   at least one principle EM beams derived from said emitted electromagnetic beam, each of said at least one principle EM beam formed of one of a plurality of series of usable series electromagnetic beams;
   at least one principle EM beam system paths that begins at said laser and terminates at a sample; wherein each of said at least one principle EM beams travels in an associated of said at least one principle EM beam system paths;
   at least one optical element rotatably associated with said platform; each of said at least one optical element being mechanically rotatably associated with said platform; wherein each of said at least one optical elements is rotatable into at least one of said at least one principle EM beam system paths; wherein each of said at least one optical elements that is rotated into one of said at least one principle EM beam system paths associated with an active of at least one of said at least one principle EM beams receives one of said usable series electromagnetic waves and emanates one of said usable series electromagnetic waves; wherein each of said at least one optical element that is rotated into one of said at least one principle EM beam system paths associated with an active of at least one of said at least one principle EM beams reduces the power of the usable series electromagnetic beams the optical element emanates relative to the power of the usable series electromagnetic beams the optical element receives; and
   an electronic data acquisition instrument configured to record output from said sample as a function of time.

2. The laser system of claim 1, wherein said at least one optical element comprises at least one polarizing optic.

3. The laser system of claim 1, wherein said emitted electromagnetic beam has a power within a first flux regime and a lower flux regime, wherein said first flux regime is an ultra-high flux regime defined as greater than about 8000 kW/m$^2$, and said lower flux regime is a fast cook-off regime defined as between about 40 kW/m$^2$ to about 400 kW/m$^2$.

4. The laser system of claim 1, wherein the power of at least one of said at least one principle EM beams at said sample is within a first flux regime and at least one of said plurality of series of usable series EM beams having a power at said sample that is within a lower flux regime than said first flux regime, wherein said first flux regime is an ultra-high flux regime defined as greater than about 8000 kW/m$^2$, and said lower flux regime is a slow cook-off regime defined as less than about 40 kW/m$^2$.

5. The laser system of claim 1, wherein one of said at least one beamsplitters is a last optical element that each of said at least one of said at least one principle EM beam travels through prior to being incident on said sample; wherein the secondary EM beam split off by said one of said at least one beamsplitters is directed to an optical detector.

6. The laser system of claim 5, farther comprising a focusing optic rotatably associated with said platform and rotatable into and out of at least one of said at least one principle EM beam system paths.

7. The laser system of claim 1 wherein said at least one optical elements comprises at least one beamsplitter, each of said at least one beamsplitter that is rotated into an active of said at least one usable series EM beams splits the usable series electromagnetic beams the beamsplitter receives into a plurality of split beams, wherein said plurality of split beams includes the usable series electromagnetic beams the optical element emanates and a secondary EM beam.

8. The laser system of claim 7, further comprising at least one beam block to absorb said secondary EM beam.

9. The laser system of claim 7, wherein said at least one optical element further comprising of at least one polarizing optic.

10. The laser system of claim 9, wherein the difference in power of said emitted electromagnetic beam and said at least one of said at least one principle EM beam incident on said sample is effected by a combination of said at least one polarizing optic and said at least one beamsplitter.

11. The laser system of claim 10, wherein one of said at least one beamsplitters is a last optical element that each of said at least one of said at least one principle EM beam travels through prior to being incident on said sample; wherein the secondary EM beam split off by said one of said at least one beamsplitters is directed to an optical detector.

12. The laser system of claim 11, further comprising a focusing optic rotatably associated with said platform and rotatable into and out of at least one of said at least one principle EM beam system paths.

13. A method of testing a sample, comprising:
emitting an electromagnetic beam from a laser mechanically associated with a platform, wherein said laser is not pulsed;
incidenting a first principle EM beam derived from said emitted EM beam onto a sample, said first principle EM beam having a power at said sample within a power region of a first flux regime of a plurality of flux regimes, wherein said first flux regime is an ultra-high flux regime defined as greater than about 8000 kW/m$^2$, said first principle EM beam propagating along one of at least one principle EM beam system path onto a sample and derived from said emitted EM beam passing through a first optical element combination of a plurality of optical element combinations; said plurality of optical element combinations formed using a plurality of optical elements rotatably associated with said platform such that each of said plurality of optical elements is rotatable into and out at least one of said at least one principle EM beam system paths;
rearranging at least one of said plurality of optical elements to form one of at least one reduced power optical element combinations and yielding at least one reduced power principle EM beams that propagates along at least one of said principle EM beam system paths and terminates at said sample, at least one of said at least one reduced power principle EM beams having a power incident at said sample within a reduced power flux regime of said plurality of flux regimes, said reduced power flux regime having a lower power than said first flux regime
wherein, in at least one of said plurality of flux regimes, said reduced power flux regime is a fast cook-off regime defined as between about 40 kW/m$^2$ to about 400 kW/m$^2$;
wherein, in at least one other of said plurality of flux regimes, said reduced power flux regime is a slow cook-off regime defined as less than about 40 kW/m$^2$; and recording output from said sample as a function of time with an electronic data acquisition instrument.

14. The method of claim 13, wherein said rearranging step is performed a plurality of times during a testing of said sample, wherein each performance of said rearranging step uses one of said at least one reduced power optical element combinations that has not been used during said testing of said sample, wherein each of said plurality of performances of said rearranging step yields one of a plurality of said at least one reduced power principle EM beams that propagates along one of said at least one principle EM beam system paths and terminates at said sample; each of said plurality of said at least one reduced power principle EM beams having a power within a single of a plurality of reduced power flux regimes; each one of said plurality of said at least one reduced power principle EM beams having a power incident on said sample that is within a different of said plurality of reduced power flux regimes than each other one of said plurality of said at least one reduced power principle EM beams, wherein each of said plurality of reduced power flux regimes has a lower power than said first flux regime.

15. The method of claim 13, wherein the power of said first principle EM beam at said sample is equal to the power of said emitted EM beam.

16. The method of claim 13, wherein said rearranging step is performed four times.

17. The method of claim 13, wherein at least one of said at least one optical element is a beamsplitter, wherein said beamsplitter is a last optical element that said first principle EM beam and each of said at least one reduced power principle EM beam travel through prior to being incident on said sample.

18. The method of claim 17, further comprising:
directing a pre-determined amount of said first principle EM beam toward an optical detector using said beamsplitter;
measuring the power of said pre-determined amount of said first principle EM beam received at said optical detector; and
determining the power of said first principle EM beam incident on said sample by using a mathematical relation of the amount of said pre-determined amount of said first principle EM beam directed toward said optical detector to an amount of said first principle EM beam incident on said sample.

19. The method of claim 18, further comprising:
directing a pre-determined amount of said at least one reduced power principle EM beams toward said optical detector using said beamsplitter;
measuring the power of said pre-determined amount of said at least one reduced power principle EM beams received at said optical detector; and
determining the power of said at least one reduced power principle EM beams incident on said sample by using a mathematical relation of the amount of said pre-determined amount of said first principle EM beam directed toward said optical detector and the amount of said first principle EM beam incident on said sample.

20. A laser system for simulating heat flux levels associated with rocket motor igniter output, comprising:
a platform;
a laser to emit an EM beam, said laser is mechanically associated with said platform, wherein said laser is not pulsed;
a plurality of positioners mechanically associated with said platform; and a plurality of optical elements, wherein each of said plurality of optical elements is associated with said platform using a corresponding of said plurality of positioners; each of said plurality of optical elements being positionable in a plurality of positions without changing a location of its corresponding positioner, wherein one of said plurality of positions is an operative position; said plurality of optical elements being arrangeable into a plurality of combinations, each of said plurality of combinations corresponding to one of at least one optical path beginning at said laser and terminating at a sample, each of said plurality of combinations corresponding to one of a plurality of distinct permutations of operatively positioned optical elements that reducingly interact with an emitted of said EM beam thereby yielding one of a plurality of versions of said emitted EM beam that is incidented upon said sample, each of said plurality of versions of said emitted EM beam that is incidented upon said sample having a lower power than said emitted EM beam; and an electronic data acquisition instrument configured to record output from said sample as a function of time.

21. The laser system of claim 20, wherein said emitted EM beam has a power within a first flux regime and at least one of said plurality of versions of said emitted beam having a power at said sample that is within a lower flux regime than said first flux regime, wherein said first flux regime is an ultra-high flux regime defined as greater than about 8000 $kW/m^2$, and said lower flux regime is a fast cook-off regime defined as between about 40 $kW/m^2$ to about 400 $kW/m^2$.

22. The laser system of claim 20, wherein said emitted EM beam has a power within a first flux regime and at least one of said plurality of versions of said emitted beam having a power at said sample that is within a lower flux regime than said first flux regime, wherein said first flux regime is an ultra-high flux regime defined as greater than about 8000 $kW/m^2$, and said lower flux regime is a slow cook-off regime defined as less than about 40 $kW/m^2$.

* * * * *